United States Patent [19]

Jerrold-Jones

[11] 4,162,211
[45] Jul. 24, 1979

[54] COMBINATION ELECTRODE ASSEMBLY

[75] Inventor: Paul Jerrold-Jones, Claremont, Calif.

[73] Assignee: Beckman Instruments, Inc., Fullerton, Calif.

[21] Appl. No.: 772,370

[22] Filed: Feb. 25, 1977

[51] Int. Cl.² ............................................. G01N 27/36
[52] U.S. Cl. ............................ 204/195 G; 204/195 F; 204/195 M
[58] Field of Search ............ 204/195 G, 195 F, 195 M

[56] References Cited

U.S. PATENT DOCUMENTS

| | | | |
|---|---|---|---|
| 2,232,211 | 2/1941 | Cary | 204/195 G |
| 3,398,079 | 8/1968 | Arthur et al. | 204/195 G |
| 3,434,953 | 3/1969 | Porter et al. | 204/195 G |
| 3,442,782 | 5/1969 | Shiller et al. | 204/195 M |
| 3,492,216 | 1/1970 | Riseman et al. | 204/195 M |
| 3,498,899 | 3/1970 | Kater et al. | 204/195 F |
| 3,510,421 | 5/1970 | Gealt | 204/195 P |
| 3,530,056 | 9/1970 | Haddad | 204/195 F |
| 3,575,834 | 4/1971 | Hoole et al. | 204/195 F |
| 3,598,712 | 8/1971 | Petersen | 204/195 G |
| 3,662,256 | 5/1972 | Eckfeldt | 204/195 G |
| 3,718,569 | 2/1973 | Petersen et al. | 204/195 G |
| 3,741,884 | 6/1973 | Deushane et al. | 204/195 G |
| 3,770,608 | 11/1973 | Kelch et al. | 204/195 M |
| 3,997,420 | 12/1976 | Buzza | 204/195 G |
| 4,012,308 | 3/1977 | Jerrold-Jones et al. | 204/195 G |
| 4,018,661 | 4/1977 | Brushwyler et al. | 204/195 G |

Primary Examiner—T. Tung
Attorney, Agent, or Firm—Robert J. Steinmeyer; Robert R. Meads; John R. Shewmaker

[57] ABSTRACT

An electrochemical combination electrode assembly having an inner, tubular glass pH electrode body supported within a tubular outer plastic container, a reference electrolyte reservoir defined in an annular space between the container and the glass electrode, and an annular, pressure contact leakage junction defined between an inclined surface and edge on the glass electrode body and plastic container for establishing electrolytic communication between the reference electrolyte and a test solution. Preferably the leakage junction is established at the junction line of an axially tapering exterior surface of the glass electrode body and a circular edge on the plastic container surrounding the tapered surface. The glass electrode is nested in the plastic container until the tapering surface and circular edge engage. The degree of pressure engagement establishes the flow rate through the junction.

6 Claims, 2 Drawing Figures

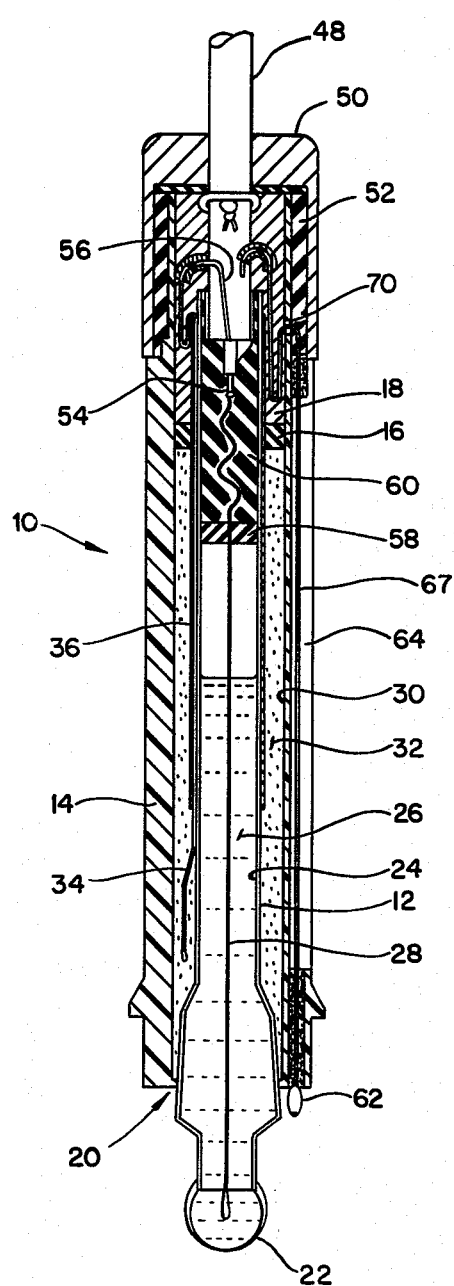
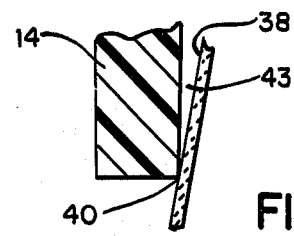
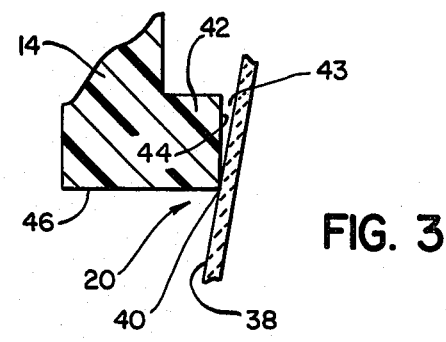
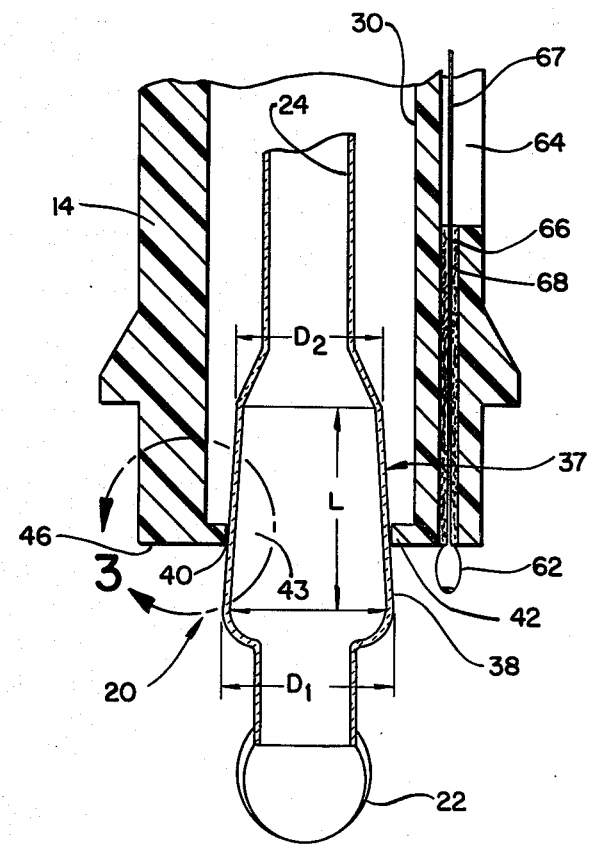
FIG. 1
FIG. 4
FIG. 3
FIG. 2

COMBINATION ELECTRODE ASSEMBLY

BACKGROUND OF THE INVENTION

1. Field of the Invention

The present invention relates generally to electrochemical electrodes and, more particularly, to combination electrodes for measuring the ion concentration of solutions.

2. Description of the Prior Art

Combination electrodes comprising a sensing portion and a reference portion are well known in the art. One known electrode assembly for measuring pH includes a tubular, glass pH electrode coaxially supported within a durable, tubular, plastic container to define an annular reference electrolyte reservoir between the electrode body and the container. In such a structure it is necessary to establish electrolytic contact between a reference electrolyte within the annular reservoir and a test solution into which the electrode is immersed. Typically this is accomplished by means of a wettable material, such as asbestos or linen fibers, which provides a minute flow rate leakage path or liquid junction between the electrolyte and the test solution. For example, the leakage path of one commercial combination electrode assembly, illustrated in copending application Ser. No. 629,833, (now U.S. Pat. No. 4,012,308) filed Nov. 7, 1975, and assigned to the assignee of the present invention, comprises a plurality of asbestos fibers spaced around and extending through an annular seal between an inner glass pH electrode body and an outer plastic container.

While asbestos fiber liquid junction structures generally function satisfactorily, they have several drawbacks and limitations. First, they require tedious operations by hand to incorporate in an electrode assembly. Second, they do not readily lend themselves to the formation of an annular liquid junction as would be desirable in combination electrodes having annular electrolyte reservoirs. Third, they can easily become clogged during use.

U.S. Pat. No. 3,492,216 (Riseman et al.) proposes a combination, ion-selective electrode assembly incorporating an annular liquid junction structure without the use of asbestos fibers or other liquid junction materials. In this regard, the electrode aseembly includes inner and outer tubular plastic bodies. The exterior surface at one end of the inner body is outwardly tapered as a frustoconical end portion. The adjacent interior surface of the outer body is conically tapered at the same angle as the frustoconical end portion so that the inner body will nest within the outer body with the tapered surfaces mating with each other and the ends of the bodies defining a planar sensing surface of the electrodes assembly. The mating tapered surfaces are roughened to establish an annular leakage path between an electrolyte reservoir within the electrode assembly and a test solution into which the assembly is to be immersed.

A similar precision-fit, annular leakage junction is described in U.S. Pat. No. 2,058,761 (Beckman et al.) for a single reference electrode and comprises a frustoconical plug seated within a glass tube to establish an annular leakage path through the contact area between the plug and the tube.

In both of the foregoing approaches, precision grinding and preparation of the mating tapered surfaces is required to establish the perfect surface area contact therebetween. Obviously, it would be desirable to provide an annular leakage path for a combination electrode in a manner which eliminates the precision manufacturing steps heretofore employed without sacrificing the durability and reliability of the electrode. The present invention meets these needs.

SUMMARY OF THE INVENTION

Briefly, and in general terms, the present invention resides in a new and improved ion sensitive combination electrode assembly of commercially practical form and incorporating an annular liquid junction which overcomes the disadvantages of the prior electrodes. The electrode assembly is simple in construction and reliable in operation and is constructed in a straightforward manner without precision manufacturing steps heretofore employed.

To these ends, the present invention comprises a combination electrode assembly including an outer tubular container and an inner electrode body of nonconductive material. The container includes an open end and an inner annular surface adjacent thereto. The electrode body is dimensioned to fit coaxially into the container through the open end thereof and includes an ion sensitive structure and an annular exterior surface adjacent thereto. One of the inner and exterior annular surfaces is inclined relative to the other and the other includes a circular edge dimensioned to engage and make line contact with the inclined surface as the electrode body is inserted into the container. The circular line contact between the edge and the inclined surface defines an annular liquid junction for the electrode assembly and the degree of pressure between the container and electrode body at the contact line determines at least in part the liquid flow rate through the junction between an electrolyte reservoir within the assembly and a test solution into which the assembly is immersed.

BRIEF DESCRIPTION OF THE DRAWING

FIG. 1 is a cross-sectional view, taken in a generally vertical plane, through a combination electrode assembly of the present invention.

FIG. 2 is an enlarged, fragmentary view of the sensing end of the assembly of FIG. 1.

FIG. 3 is an enlarged, fragmentary view of the portion of the assembly denoted by the line 3 in FIG. 2 and illustrates the line contact liquid junction structure of the present invention.

FIG. 4 is a view similar to FIG. 3 of another embodiment of the invention.

DESCRIPTION OF THE PREFERRED EMBODIMENTS

As shown in the drawing for purposes of illustration, the invention is embodied in an ion sensitive, combination electrode assembly, indicated generally by numeral 10. The electrode assembly 10 comprises an indicating electrode 12, of generally tubular configuration, supported near its opposite ends to extend coaxially within a generally tubular outer container 14 formed of a durable nonconductive material such as polyethylene, polypropylene, or a fluorocarbon plastic. Container 14 could also be made of glass. As illustrated in FIG. 1, the support for the upper end of electrode 12 within container 14 comprises an elastomeric sleeve-like structure of silicone rubber including an annular sealing band 16 and an adhesive layer 18 disposed in an annular space between the electrode and the container. The support for the lower end of the electrode comprises a novel annular junction, indicated generally by numeral 20, between the electrode 12 and container 14.

For measuring pH, the indicating electrode 12 comprises a generally tubular, glass electrode body the lower or sensing end of which is closed by a spherical membrane 22 of pH sensitive glass. The interior of the indicating electrode 12 defines a first or internal electrolyte reservoir 24 immediately adjacent membrane 22 and filled with a suitable electrolyte 26, such as an aqueous solution of potassium chloride. A conventional indicating half cell 28 comprising a silver wire conductor coated at its lower end with silver chloride extends axially into the internal reservoir and is immersed in the electrolyte 26.

The annular space above the annular junction 20 and between the exterior of the electrode 12 and the interior of the container 14 defines a second or reference electrolyte reservoir 30 filled with a second or reference electrolyte 32, such as potassium chloride. In the preferred embodiment, electrolyte 32 includes a gelling agent to minimize electrolyte loss during operation of the assembly. A conventional reference half cell 34 comprising a silver wire conductor coated at its lower end with silver chloride extends axially into the reference electrolyte reservoir and is immersed in the electrolyte 32. The reference half cell is retained for a major portion of its length between electrode 12 and a conductive heat-shrink tube 36 coaxially circumscribing and secured by a shrink fit to the electrode 12.

In accordance with a primary aspect of the present invention, the annular junction 20 supporting the electrode 12 within the container 14 also provides an improved liquid junction structure for establishing a leakage path between the reference electrolyte 32 within the electrode assembly and a test solution into which the electrode assembly is immersed. To this end, and in one form of the invention only, a section 37 (FIG. 2) of the tubular glass electrode body 12 tapers outwardly from the electrode axis to provide an axially and outwardly tapering surface 38 near the sensing end of the glass electrode 12. As illustrated, the enlarged section 37 of the electrode 12 presents a substantially frustoconical tapering exterior surface 38 extending axially a distance L along the electrode body and varying in diameter between first and second values, $D_1$ and $D_2$. In the preferred embodiment, surface 38 tapers at an angle of about 10° with respect to the electrode longitudinal axis.

The glass electrode 12 is supported within tubular container 14 by an edge 40 on an internal surface of the container coaxially surrounding and engaging the tapered surface 38 of the electrode 12. As illustrated in FIG. 2, the lower end of tubular container 14 includes an inwardly projecting, annular collar 42 which defines a circular opening 43 within the end of the container for receiving electrode 12. Significantly, and as illustrated in FIG. 3, collar 42 has an axially extending, inwardly facing, substantially cylindrical surface 44 inclined with respect to the axially tapering surface 38. The cylindrical inner surface 44 terminates at a flat lower surface 46 of the collar to define the circular edge 40. The tapering surface 38 of electrode 12 is engaged by the edge 40 to establish a circular line contact junction between the frustoconical section 37 and the container 14.

Significantly, the annular junction 20 can be located at any point along the length L of tapered surface 38. For this purpose, the diameter of the opening 43 in the end of container 14 may have any value between the diameter values $D_1$ and $D_2$ of tapered surface 38. As the diameter of opening 43 approaches $D_1$, the annular junction 20 will be located progressively toward the lower end of the tapered surface. Because of the tolerance in the diameter of opening 43, no precision machining or grinding is required to establish a proper fit between and support for the electrode body 12 within the container 14. Representative dimensions in the preferred embodiment are L=0.40 in. and $D_1$=0.32 in. Collar 42 extends inwardly 0.06 in. from the interior wall of container 14, and cylindrical surface 44 of the collar extends 0.075 in. in the direction of the electrode axis.

In the preferred embodiment, the edge 40 engaging the tapered surface 38 is located at a lower inner corner of the collar 42. The collar is slightly compliant and when the electrode 12 and container 14 are nested, the collar flexes slightly around its annular periphery thereby securely seating against tapered surface 38. However, if desired, and to further simplify construction of tubular container 14, collar 42 may be eliminated as illustrated in FIG. 4. In such an embodiment, the diameter of the interior wall of container 14 may be reduced to a value intermediate the $D_1$ and $D_2$ values allowing the lower inner circular edge of the container to function as the circular edge 40 engaging the surface 38 of electrode 12 and establish the liquid junction 20.

Applicant has discovered that a controllable liquid leakage path is provided by the annular junction 20 between electrolyte 32 within the electrode assembly and a test solution. In this regard, the rate of flow through the annular junction 20 may be controlled by adjusting pressure between surface 38 and edge 40 during assembly of the electrode. The degree of pressure between surface 38 and edge 40 is originally established by trial and error. With minimal practice, an assembler can establish the necessary pressure engagement simply by feel as the parts are engaged. Further, it has been found that the flow rate through annular junction 20 can be controlled by the characteristics of the junction forming surfaces. In this regard, it has been found desirable to abrade tapered surface 38. This may be accomplished by rubbing the surface with a number 3F carborundum or aluminum oxide emory cloth or by sand blasting or chemical etching of the surface.

To complete the illustrated electrode assembly 10, the upper end thereof is closed and electrical connections are made to the indicating and reference half cells 28 and 34 in a conventional manner. For this purpose a conventional shielded coaxial cable 48 containing a plurality of conductors insulated from each other extends through the base of a conductive metal cap 50 into the upper end of tubular container 14. The cap 50 includes side wall portions coaxially surrounding the upper end of container 14 and secured thereto by a layer of epoxy adhesive 52.

Coaxial cable 48, which connects the electrode assembly 10 to a pH or other measuring system, includes a center conductor 54 soldered to indicating half cell 28 and a second conductor 56 soldered to reference half cell 34. If desired, an insulating shrink tube may be secured in place around the solder connections to electrically insulate the same.

Annular sealing band 16 seals reference electrolyte 32 in the annular reservoir 30. If desired, sealing band 16 may directly contact the electrolyte to prevent formation of air bubbles in the reservoir. A sealing disc or plug 58 closes the top of the internal electrolyte reservoir 24 and may similarly contact electrolyte 26 therein, if desired. A space within glass electrode body 12 above sealing disc 58 is filled with an epoxy sealing material 60 which is cured to secure the sealing disc in place and to insulate and mechanically strengthen the solder connection between half cell 28 and center conductor 54 of the coaxial cable. In a similar manner, the sealing material 18 at the upper end of the annular reservoir 30 above band 16 holds the band in place and insulates and mechanically strengthens the remaining electrical connections to the coaxial cable. In addition, this sealing material further serves to secure electrode 12 and container 14 in a fixed relative axial position after establishment of the desired annular junction 20 at the sensing end thereof.

In accordance with another aspect of the present invention, the electrode assembly 10 includes an integral thermal sensing element 62. The element combines with external circuitry (not shown) to compensate for variations in temperature of the test solution. As is well known, the voltage developed by a pH electrode is a function of temperature. Thermal sensing element 62 includes a conventional thermistor covered with a protective layer of epoxy and disposed adjacent the sensing end of the electrode assembly 10. For this purpose, the wall of tubular container 14 includes an axially extending slot or passage 64 extending most of the length of the tubular container for receiving first and second leads of the thermistor 62. At its lower end, slot 64 communicates with a bore 66 through the remainder of the axial length of the container wall. Thermistor 62 is disposed at the bottom of container 14 with first and second conductor leads (only one such conductor 67 is illustrated) extending therefrom upwardly through bore 66 and slot 64 to the upper end of the electrode assembly. Bore 66 is filled with an epoxy adhesive 68 for securing the thermistor in place. Preferably, each conductor of the thermistor is sheathed within an insulating plastic tube to ensure adequate insulation between the conductors. The conductors extend through a small port 70 in the wall of tubular container 14 and are solder connected to respective insulated conductors of the coaxial cable assembly 48. The connection for conductor 67 is illustrated in FIG. 1. After the thermistor 62 is electrically connected to the coaxial cable 48, slot 64 may be filled with a sealing compound, such as epoxy, to protect the conductors therein.

Thermal sensing element 62 and its associated circuitry (not shown) provide rapid thermal compensation of the electrode assembly 10 since the thermal element directly contacts the test solution in which the electrode assembly is immersed and responds directly and rapidly thereto. Significantly, the thermal sensing element is provided integral with the electrode assembly without any attendant increase in size or complexity of the assembly.

While the basic structure of the electrode assembly 10 has been described hereinabove, an even clearer appreciation of the simplicity and novel features of the invention and its manufacture may be achieved from a consideration of the manner of assembly of the invention. In this regard, thermistor 62 is first dipped in epoxy and the epoxy allowed to cure. Thereafter, two pieces of polyethylene tubing (60 clay adams) are slipped over the respective thermistor leads and the thus insulated leads are fed through bore 66 in tubular container 14 until the sensing element is positioned at the end of the container. Epoxy adhesive 68 is injected into the bore 66 and allowed to cure to secure the sensing element 62 in place. The two conductors are then pulled tight and the upper ends thereof inserted through passage 70 into the interior of container 14.

Next, glass electrode body 12 with its outwardly tapered section 38 is formed using well known glass blowing techniques. Thereafter, pH sensitive glass bulb 22 is fused to the lower end of body 12.

Conventional indicating and reference half cells 28 and 34 are provided. Half cell conductor 34 is positioned on the outside of glass electrode 12 with its lower end just short of tapered surface 38. Conductive heat shrink tubing 36 is slipped over the electrode 12 and the half cell 34 and is shrunk in place with a portion of the half cell protruding from the bottom of the shrink tube.

The internal electrolyte reservoir 24 of electrode 12 is filled with a potassium chloride electrolyte solution. Indicating half cell 28 is inserted through sealing disc 58 and the half cell 28 and the sealing disc are inserted together into the electrolyte reservoir 24 with the half cell immersed in the electrolyte. Part of the volume within the glass tube above sealing disc 58 is filled with a sealing adhesive 60 which is cured to hold sealing disc 58 in place.

Next the tubular plastic container 14 is slipped over the upper end of the glass electrode 12 and telescoped axially therealong until the edge 40 on inwardly projecting collar 42 engages tapered surface 38 in proper pressure engagement therewith. As indicated, this is a simple and straightforward operation for forming annular pressure contact junction 20 and is readily mastered by a semi-skilled assembler.

Annular reservoir 32 is then filled with a potassium chloride electrolyte and sealing band 16 is positioned between electrode 12 and container 14 to center the electrode within the container and to seal the reference electrolyte reservoir 30. A small volume above sealing band 16 is filled with epoxy which is cured to hold the band in place.

Finally, electrical connection is made with the electrode assembly 10. In this regard, the indicating half cell 28 is soldered to center conductor 54 of coaxial cable 48. Reference half cell conductor 34 is soldered to twined strands 56 from the shielding layer of the cable. The conductive leads from thermistor 62 are similarly soldered to respective conductors of the coaxial cable. Each solder connection may be covered with an insulating shrink tube to adequately electrically insulate the connection.

The remaining volume within the top of electrode 12 is filled with epoxy and the cable 48 and soldered center conductor 54 thereof are pushed into the epoxy filled end of electrode 12. Thereafter, the remaining cavity within the upper end of tubular container 14 above sealing band 16 is filled to the top of container 14. The epoxy thus introduced into electrode 12 and container 14 is allowed to cure while keeping cable 48 straight. After curing, cap 50 is located over the end of the electrode assembly 10 and secured by adhesive 52. As assembled, the electrode assembly is approximately 5.5 inches in length and 0.65 inch in diameter.

From the foregoing it is evident that the electrode assembly 10 is extremely simple in design and in manner of assembly. The annular junction 20 is provided as a circular pressure contact junction between a circular edge and an inclined surface on different ones of the inner electrode body 12 and the tubular container 14.

The junction is, in effect, selfadjusting during assembly to seat and locate the annular junction 20 at a position along the length L of the tapered surface 38 within a range of possible positions. The exact location is not critical and precision machining or grinding of corresponding surfaces to critically locate the annular junction is unnecessary. Moreover, the electrode assembly provides an integral thermal sensor for directly contacting the test solution to compensate for temperature variations of the solution.

While a preferred embodiment of the invention has been illustrated and described, various modifications can be made therein without departing from the scope of the invention as defined in the following claims.

What is claimed is:

1. An electrochemical combination electrode assembly comprising:
    an outer tubular container of nonconductive material having an inner annular surface adjacent an open end thereof;
    an elongated electrode body of nonconductive material coaxial with said open end of said container and having an ion sensitive structure closing one end thereof and an annular exterior surface adjacent said ion sensitive structure;
    one of said inner and exterior surfaces being inclined relative to the other and inclined relative to an intersecting surface which intersects said other surface defining at the intersection thereof a circular edge dimensioned to engage and make line contact with the inclined one of said surfaces as said electrode body is coaxially inserted into said container; and
    an annular liquid junction for said electrode assembly defined by said circular edge in pressure contact with said inclined surface, the degree of pressure between said edge and said inclined surface determining at least in part the rate of flow of liquid through said junction.

2. The electrode assembly of claim 1 wherein said inclined surface is axially inclined and is frustoconical.

3. The electrode assembly of claim 2 wherein said circular edge is defined by an annular inwardly extending collar of said outer tubular container.

4. The electrode assembly of claim 2 wherein said inclined surface is roughened to provide a wettable surface for the passage of liquid by said liquid junction.

5. An electrochemical combination electrode assembly comprising:
    a first elongate, generally tubular, nonconductive electrode body having an ion sensitive structure closing one end thereof, said body having an exterior surface portion intermediate the ends of said body which coaxially surrounds an axis of said body and which tapers in the axial direction at an angle with respect to said axis whereby the diameter of the tapered surface in a direction normal to said axis progressively varies from a first to a second value;
    a second elongate, generally tubular, nonconductive container body coaxially surrounding said first body and spaced therefrom to define an electrolyte reservoir therebetween, said second body having intersecting surface portions coaxially surrounding said axis and said tapered exterior surface of said first body, said intersecting surface portions being disposed at different respective angles to said axis than that of said tapered exterior surface portion and having a diameter at the intersection thereof in said normal direction intermediate said first and second values; and
    an annular leakage path at a junction of said tapered and said intersecting surface portions of said first and second bodies for providing electrolytic communication between said electrolyte reservoir and a test solution.

6. The electrode assembly of claim 5 wherein said tapered surface portion is frustoconical and said intersecting surface portions defined a circular edge at the intersection thereof for making line contact with said tapered surface to define said leakage path.

* * * * *